United States Patent [19]

Loucks et al.

[11] Patent Number: 4,990,456

[45] Date of Patent: Feb. 5, 1991

[54] ANALYSIS OF ASPHALT

[75] Inventors: Dennis A. Loucks, Bright's Grove; Frederick P. Seguin, Sarnia, both of Canada

[73] Assignee: Polysar Limited, Sarnia, Canada

[21] Appl. No.: 264,868

[22] Filed: Oct. 31, 1988

[51] Int. Cl.$^5$ ............................................. G01N 33/00
[52] U.S. Cl. ....................................... 436/139; 55/67; 436/161; 436/174
[58] Field of Search ............... 55/67; 73/23.1; 436/83, 436/139, 161, 174

[56] References Cited

U.S. PATENT DOCUMENTS

| | | | |
|---|---|---|---|
| 3,719,084 | 3/1973 | Walker | 73/23.1 |
| 4,728,344 | 3/1988 | Stacy | 55/67 |

Primary Examiner—Charles Hart
Attorney, Agent, or Firm—Stevens, Davis, Miller & Mosher

[57] ABSTRACT

The rubber content in a low gel rubber modified asphalt may be accurately and rapidly determined using gel permeation chromatography in which one or more columns comprise glass particles having a size from 80/120 mesh to 200/400 mesh and a pore size from 75 to 120A. The analysis may be automated and is faster and more accurate than currently used procedures.

13 Claims, 1 Drawing Sheet

ANALYSIS OF ASPHALT

FIELD OF THE INVENTION

The present invention relates to a method for determining the low gel polymer content in polymer modified asphalt, bitumen, tar, or a mixture thereof.

BACKGROUND OF THE INVENTION

Asphalt has a broad range of applications from roofing to paving. With the increasing costs of asphalt, bitumen, tar or mixtures thereof, it is becoming cheaper over the long term to modify such materials with relatively small amounts of polymers. This tends to improve the properties of asphalt, bitumen, tar and mixtures thereof at temperatures in excess of 135° F. (e.g. estimated road temperature in Arizona on a hot day) and at temperatures below about 40° F. Generally, the high temperature rheology of the asphalt, bitumen, tar or a mixture thereof is improved (decreased flow) and the ductility of such materials at lower temperatures is also improved by polymer modification. As a result of the high cost of roofing and paving it is becoming economically advantageous to extend the life of products made with such material by modifying them with various polymers. While a premium price may be charged for polymer modified asphalt, bitumen, tar or a mixture thereof, it is extremely difficult to analyze the modified material to determine the presence and quantity of polymer. This has lead to the adoption of various indirect tests such as ductility (elongation tests) penetration tests, and torsional recovery tests (such as the test used by the California Highways Dept.—CAL 332). Unfortunately, this indirect test is prone to vary depending on the type and grade of asphalt, bitumen, tar or a mixture thereof which is used as a base. Thus, a polymer modified asphalt, bitumen, tar or mixture thereof may behave as if it is not polymer modified and a non-modified ashpalt, bitumen, coal tar or a mixture thereof may behave as if it is modified. This makes it extremely difficult for manufacturers and customers to provide quality control. To the best of applicants' knowledge there is no simple test to directly measure the polymer content in polymer modified asphalt, bitumen, tar or a mixture thereof.

There are a number of patents relating to various designs of gel permeation chromatographs (GPC's) such as U.S. Pat. No. 4,728,344 issued Mar. 1, 1988 assigned to Philips Petroleum which discloses a heated GPC. However, the Patent does not suggest using such a device to detect and quantify the polymer in polymer modified asphalt, bitumen, tar or a mixture thereof.

U.S. Pat. No. 3,719,084 issued Mar. 6, 1978, assigned to McDonnell Douglas discloses the use of a gas chromatograph to separate and/or identify complex mixtures of organic materials containing 1 to 20 carbon atoms. The polymers used to modify asphalt bitumen, tar and mixtures thereof contain more than 20 carbon atoms.

Commercially available columns for this application of gel permeation chromatography are STYRAGEL(-Trademark—styrene-divinyl benzene gel) typically having a pore size from about 500 to 10,000 A. Such columns tend to plug if used to analyze polymer modified asphalt, bitumen, tar or a mixture thereof. Controlled pore glass is known but its suggested uses include separating protein molecules, viruses, cell components, and polymers having a molecular weight from $10^3$ to $10^{10}$. It has not been proposed to use such columns to separate polymers from asphalt, bitumen, tar or a mixture thereof.

SUMMARY OF THE INVENTION

The present invention provides a process for determining the low gel polymer content in a polymer modified asphalt bitumen, tar or a mixture thereof essentially consisting of asphalt, bitumen, tar or a mixture thereof having an average molecular weight less than $10^{4.5}$ and polymeric components having an average molecular weight of at least $10^3$ comprising:

(a) dissolving polymer modified asphalt in a suitable solvent;

(b) passing a sample of the resulting solution through a gel permeation chromatograph in which one or more chromatograph columns comprise a controlled pore glass column in which the glass particles have a size from 80/120 mesh to 200/400 mesh and a maximum pore size in the range 75 to 120A; and (c) detecting and quantifying the low gel polymer and the asphalt portions of the solution as they leave as the chromatograph column.

DETAILED DESCRIPTION OF THE INVENTION

Figure 1:
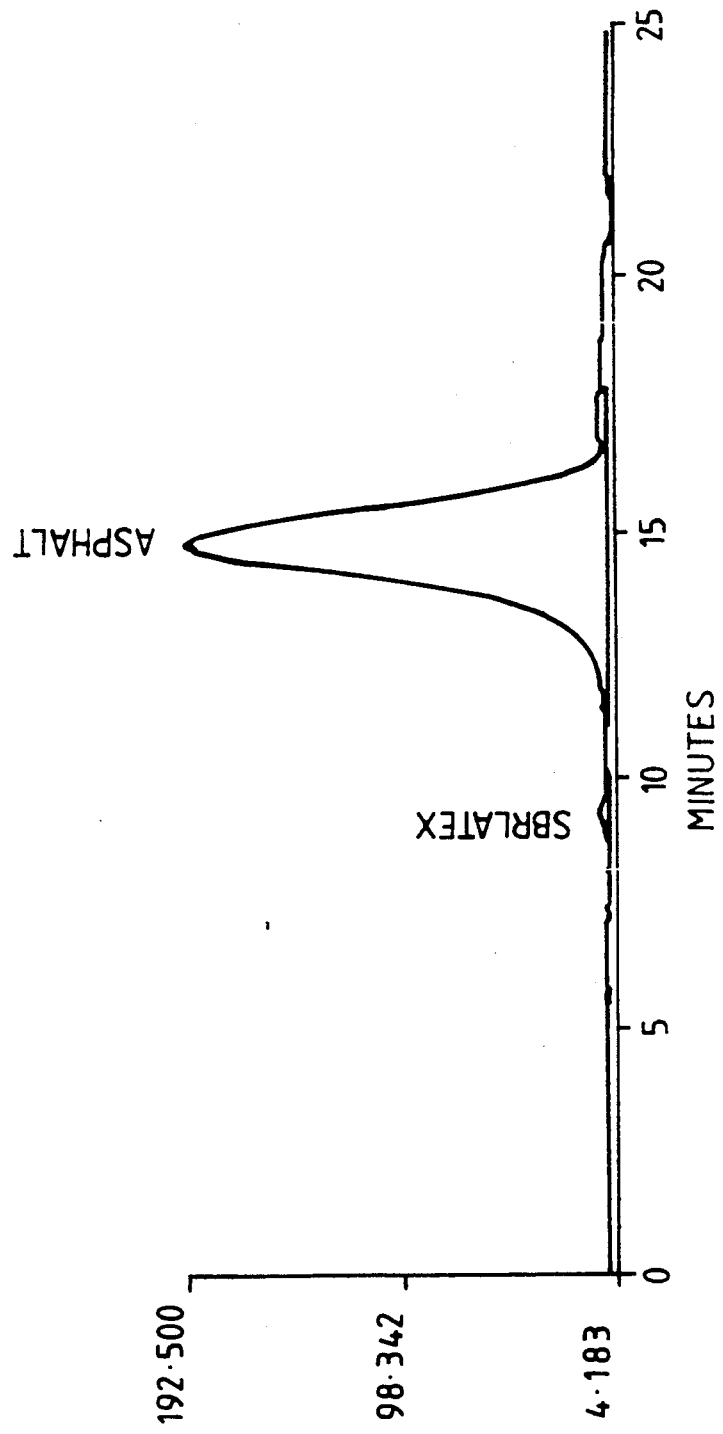

FIG. 1 is a typical chromatograph obtained in accordance with the present invention.

As used in this specification the term low gel polymer means a polymer of which at least 70, preferably more than 85, most preferably more than 90 weight percent is totally soluble in a solvent selected from the group consisting of tetrahydrofuran, toluene, and benzene.

The asphalt, bitumen, tar or a mixture thereof which may be analyzed in accordance with the present invention should comprise a mixture of components which have a molecular weight not exceeding about $10^{4.5}$, preferably from about $10^2$ to $10^4$, most preferably less than $10^3$.

The polymers which are useful in accordance with the present invention may be selected from a broad range of polymers including: styrene butadiene (SB) rubbers, acrylonitrile butadiene (NBR) rubbers, polybutadienes, butyl rubbers, ethylene-propylene (EP) rubbers, ethylene-propylene-diene (EPDM) rubbers, natural rubber, acrylates and vinyl acrylate copolymers. These polymers may contain small amounts, typically not more than 10, preferably less than 5, weight percent in total of the polymer of the residue of polymerizable functional monomers such as ethylenically unsaturated carboxylic acids such as acrylic, methacrylic, fumaric and itaconic acid; ethylenically unsaturated aldehydes such as acrolein; esters of ethylenically unsaturated acids such as methyl, ethyl, hydroxyethyl, butyl, hexyl and ethylhexyl acrylates and methacrylates; amides of ethylenically unsaturated carboxylic acids such as acrylamide, methacrylamide, and N-methylol acrylamide; and vinyl esters of saturated acids such as vinyl acetate.

It should be noted that functional monomers will increase the polarity of the polymer which will increase polymer residence time as it passes through the column. At low levels of functional monomers such as less than 10, most preferably less than 5 weight percent this should not interfere with the process of the present invention.

The polymers used to modify the asphalt, bitumen, tar or a mixture thereof should have an average molecular weight of at least $10^3$ preferablly greater then $10^4$.

The polymer modified asphalt, bitumen, tar or mixture thereof is dissolved in a suitable solvent. The solvent must be capable of dissolving the asphalt, bitumen, tar or mixture thereof and also capable of dissolving the polymer. Typically, the solvent will be a hydrocarbon solvent containing from about 3 to 10 carbon atoms. The solvent may contain a heteroatom such as oxygen or nitrogen. Preferred hydrocarbon solvents include tetrahydrofuran, cyclohexane, benzene and toluene. It is desirable to include a small amount of a polar solvent in an amount up to about 3, preferably less than 1, weight percent of the total solvent. Useful polar solvents include $C_{1-4}$ alcohols and water. The preferred polar solvent is water. Care should be taken as a lack of polar solvent may cause peak tailing introducing error into the analysis.

The solution of polymer modified asphalt, bitumen, tar or a mixture thereof is prepared in a very dilute form. Preferably less than 1.0, most preferably 0.5 or less percent w/v of sample is dissolved in 99.5%/w/v of solvent. Very small samples of the resulting solution, preferably less than 500, most preferably 200 or less $\mu l$ are analyzed using the chromatograph.

The chromatograph columns used in accordance with the present invention are controlled pore glass (CPG) columns which have a maximum pore size of 75-120A. A 120A pore size will have a range of pore sizes from 105 to 135A. Most preferably, the pore size is small such as 75A which will have pore sizes in the range from 65 to 85A. The glass beads which form the column should have a particle size so that they will pass through a 200/400 mesh (37-74 micron diameter) to those which will pass through an 80/120 mesh (125-177 microns). The larger the particle size the faster the sample will pass through the column(s). Preferably the column will comprise an 80/120 mesh (125-177 micron) particles having a 65 to 85A pore size distribution (e.g. 75A pore size).

While the column may be packed with a mixture of pore sizes, it is preferable to separate columns in sequence. The columns having a series of pore sizes from 105-135A to 65-85A are useful. A particularly useful series of columns comprises a first columns packed with CPG having a pore size of 105-135A and second and third columns packed with CPG having a pore size of 65-85A.

When the sample of solution of polymer modified asphalt, bitumen or tar passes through the columns, it is separated by molecular size. The largest molecules pass through the columns fastest and the smaller molecules pass through the columns slowest. Thus, the polymer will leave the GPC columns first. At the exit from the columns there is a suitable detector. Preferably, the detector comprises a differential refractive index dectector. The detector should be used in conjunction with a quantifying means. Preferably, the signal from the differential refractive index detector is digitized and fed to a computer. The computer then generates a graph of the amount of material passing through the column with the area under the graph being proportional to the relative amount of material in the sample. Preferably, the computer will integrate the areas under the graph. Suitable computers and software are available. A particularly useful computer software package is marketed by the Waters Company (e.g. Waters 840).

Alternately a series of calibration curves for known polymer/asphalt blends may be prepared. Then the analysis need only be made for the polymer peak. The quantity of polymer is determined from the calibration curves. This method is independent of asphalt.

While the polymers analyzed in accordance with the present invention should have a low gel content, it is possible to analyze samples with a higher gel content. This is possible only if samples of the polymers are provided to the analytical lab together with asphalt. Then the gel (in solubles) content of the polymer may be determined and the ratio of asphalt to polymer corrected for the insoluble content of the polymer. This is not recommended for routine use because the higher molecular weight portions of polymer may eventually accumulate requiring replacement of the guard column(s). Preferably, the present invention is operated in conjunction with an automatic sampler. That is, a tray of a large number of cells (e.g. up to 96) is loaded cooperatively with the sampler. The sampler then automatically in sequence samples each cell and runs the GPC. The advantage of this system is the automated system can run the GPC and computer on "off" hours such as overnight. In the morning the analyses are available. This permits a large number of samples to be analyzed rapidly. Compared to the torsional recovery test CAL 332 the present method is more accurate and has higher productivity.

The following examples are intended to illustrate the invention and not to limit the invention. In the examples, unless otherwise specified, parts are by dry weight.

EXAMPLE 1

In a separate laboratory a series of styrene butadiene rubber (SBR) modified asphalt emulsions were prepared. On a dry basis the asphalt contained 1, 3, and 5 percent SBR. Additionally, two unknowns were also prepared. The samples were dissolved in tetrahydrofuran/1% water in 0.5% w/v ratio. 200 $\mu l$ volumes of the resulting solution of each sample were then injected into a Waters GPC. Three columns two feet long having a $\frac{1}{4}''$ outer diameter were used in series. The first column was packed with control pore size glass beads having a pore size of 120A. The second and third columns were packed with control size glass having a pore size of 75A. All the control pore size glass had a particle size of 200/400 mesh (37-74 microns). The GPC used a differential refractive index detector.

The chromatogram from the first unknown is shown in FIG. 1. From the chromatograms the measured amount of SBR were:

1.022%
2.900%
5.086%
1.671% (unknown)
2.900% (unknown)

The unknown values were prepared at 1.75 and 3 weight percent SBR. These results show a good (better than presently available) analytical result. By way of comparison Cal 233 uses a torsional recovery test to try to detect the presence and approximate quantity of polymer.

What is claimed is:

1. A process for determining the low gel polymer content in a polymer modified asphalt, bitumen, tar or a mixture thereof essentially consisting of asphalt, bitumen, tar or a mixture thereof having an average molecular weight less than $10^{4.5}$ and polymeric components having an average molecular weight of at least $10^3$ comprising:

(a) dissolving polymer modified asphalt in a suitable solvent;

(b) passing a sample of the resulting solution through a gel permeation chromatograph in which one or more chromatograph columns comprise a controlled pore glass column in which the glass particles have a size from 80/120 mesh to 200/400 mesh and a maximum pore size in the range 75 to 120A; and (c) detecting and quantifying the low gel polymer and the asphalt portions of the solution as they leave the chromatograph column.

2. A process according to claim 1 wherein the asphalt, bitumen, tar or a mixture thereof has a molecular weight of less than $10^3$.

3. A process according to claim 2 wherein the polymeric components have an average molecular weight from $10^4$ to $10^5$.

4. A process according to claim 3 wherein the low gel polymer and asphalt portions of the solution are detected as they leave the chromatograph column using a differential refractive index detector.

5. A process according to claim 4 wherein the low gel polymer and asphalt portions of the solution are quantified by digitizing the output signals from the differential refractive index detector using a computer means and generating a graph in which the areas under the curve for the low gel polymer and the curve for asphalt are proportional to their relative amounts.

6. A process according to claim 4 where in the low gel polymer content in the solution is quantified and compared to a calibration curve.

7. A process according to claim 4 wherein said controlled pore glass column has a pore size from 105 to 135A.

8. A process according to claim 2 wherein said controlled pore glass column has a pore size from 65 to 85A.

9. A process according to claim 4 wherein said chromatograph comprises three sequential columns, the first having a pore size from 105 to 135A and the second and third having a pure size from 65 to 85A.

10. A process according to claim 4 wherein said low gel polymer is selected from the group consisting of styrene butadiene polymers, ethylene-propylene-diene polymers, acrylonitrile butadiene polymers and acrylates.

11. A process according to claim 4 wherein said solvent comprises tetrahydrofuran containing up to about 3 weight percent of a polar liquid.

12. A process according to claim 11 wherein said polar liquid is selected from the group consisting of $C_{1-4}$ alkanols, water a mixture thereof.

13. A process according to claim 4 wherein solutions of polymer modified asphalt, bitumen, tar or a mixture thereof are placed in a multi-celled sample tray and placed to cooperate with an automatic sampler.

* * * * *